United States Patent
Carpenter et al.

(10) Patent No.: US 11,020,613 B2
(45) Date of Patent: Jun. 1, 2021

(54) PHYSICIAN DIRECTED RADIATION TREATMENT PLANNING

(71) Applicant: Siris Medical, Inc., Burlingame, CA (US)

(72) Inventors: Colin Morehouse Carpenter, San Carlos, CA (US); Ran Davidi, Sunnyvale, CA (US); Adam J. Pattison, San Mateo, CA (US)

(73) Assignee: SIRIS MEDICAL, INC., Burlingame, CA (US)

( * ) Notice: Subject to any disclaimer, the term of this patent is extended or adjusted under 35 U.S.C. 154(b) by 235 days.

(21) Appl. No.: 16/378,149

(22) Filed: Apr. 8, 2019

(65) Prior Publication Data

US 2019/0299024 A1    Oct. 3, 2019

Related U.S. Application Data (63) Continuation of application No. 14/930,522, filed on Nov. 2, 2015, now Pat. No. 10,293,179.

(60) Provisional application No. 62/073,711, filed on Oct. 31, 2014.

(51) Int. Cl.
*A61N 5/10* (2006.01)

(52) U.S. Cl.
CPC ...... *A61N 5/103* (2013.01); *A61N 2005/1041* (2013.01); *A61N 2005/1074* (2013.01)

(58) Field of Classification Search
CPC .... A61N 2005/1041; A61N 2005/1074; A61N 5/103
See application file for complete search history.

(56) References Cited

U.S. PATENT DOCUMENTS

| | | | |
|---|---|---|---|
| 6,038,283 A | 3/2000 | Carol et al. | |
| 6,327,490 B1 | 12/2001 | Spetz | |
| 6,560,311 B1 | 5/2003 | Shepard et al. | |
| 6,719,683 B2 | 4/2004 | Fröhlich | |
| 7,046,762 B2 | 5/2006 | Lee | |
| 7,206,377 B2 | 4/2007 | Svatos | |
| 7,593,505 B2 | 9/2009 | Saracen et al. | |
| 7,611,452 B2 | 11/2009 | Allison et al. | |
| 7,820,989 B2 | 10/2010 | Sommer | |
| 7,876,882 B2 | 1/2011 | Meyer et al. | |
| 8,121,252 B2 | 2/2012 | Nord et al. | |
| 8,144,833 B2 | 3/2012 | Breedveld | |
| 8,199,990 B2 | 6/2012 | Foshee et al. | |
| 8,222,616 B2 | 7/2012 | Lu et al. | |
| 8,232,535 B2 | 7/2012 | Olivera et al. | |

(Continued)

FOREIGN PATENT DOCUMENTS

| | | |
|---|---|---|
| WO | 2013/049845 A2 | 4/2013 |
| WO | 2014/205386 A1 | 12/2014 |

*Primary Examiner* — Christine H Matthews
(74) *Attorney, Agent, or Firm* — Artegis Law Group, LLP (57) ABSTRACT

The treatment planning engine empowers radiation treatment decision makers, such as a physician, to efficiently identify effective radiation treatment outcomes for a given patient during the contouring stage. Specifically, using the treatment planning engine, the physician may iteratively and in real-time evaluate different treatment outcomes for a patient before selecting an optimal outcome that will guide the delivery of radiation treatment to the patient. By providing real-time information as to potential toxicity and treatment efficacy during the contouring stage, the physician is empowered to make informed decisions at the preliminary contouring stage.

24 Claims, 6 Drawing Sheets

(56) References Cited

U.S. PATENT DOCUMENTS

| | | |
|---|---|---|
| 8,363,784 B2 | 1/2013 | Sobering et al. |
| 8,688,618 B2 | 4/2014 | McNutt et al. |
| 2011/0124976 A1 | 5/2011 | Sabczynski et al. |
| 2011/0130614 A1 | 6/2011 | Schulz et al. |
| 2011/0153547 A1 | 6/2011 | McNutt et al. |
| 2012/0059252 A1 | 3/2012 | Li et al. |
| 2012/0136194 A1 | 5/2012 | Zhang et al. |
| 2012/0184841 A1 | 7/2012 | Nielsen et al. |
| 2012/0310615 A1 | 12/2012 | Moore et al. |
| 2013/0072742 A1 | 3/2013 | Nord et al. |
| 2013/0191146 A1 | 7/2013 | Park et al. |
| 2013/0272593 A1 | 10/2013 | Lee et al. |
| 2014/0019440 A1 | 1/2014 | Kim et al. |
| 2014/0378736 A1 | 12/2014 | Fox et al. |
| 2014/0378737 A1 | 12/2014 | Carpenter et al. |

| | Patient 25 — 304 | Patient 23 — 306 |
|---|---|---|
| Larynx Mean | 22.6 | 27.5 |
| PTV63 | 94.8 | 95.2 |
| Ips Parotid Mean | 28.8 | 27.4 |
| Stem Max | 38.4 | 35.7 |
| Cord Max | 40.3 | 39.0 |
| Cord +5mm Max | 45.2 | 44.2 |
| Mandible Max | 59.6 | 59.8 |
| Constrictor Mean | 33.3 | 37.1 |
| Oral_Cavity Mean | 12.6 | 20.7 |
| PTV60 | N/A | N/A |
| PTV54 | 96.0 | 95.6 |

PHYSICIAN DIRECTED RADIATION TREATMENT PLANNING

CROSS REFERENCE TO RELATED APPLICATIONS

This application is a continuation of U.S. patent application Ser. No. 14/930,522, filed on Nov. 2, 2015, which claims the benefit of U.S. Provisional Application No. 62/073,711, filed Oct. 31, 2014, each of which are incorporated herein by reference in their entireties for all purposes.

BACKGROUND

This invention relates generally to radiation treatment planning.

Providing radiation therapy to patients diagnosed with cancer includes creating a radiation treatment outcome. Often, where the cancer is localized in the patient's anatomy, such as in a tumor, the creation of the radiation treatment outcome involves solving a difficult geometric problem and/or making judgment calls related to the total radiation dose or total dose received by the tumor and nearby healthy tissue. Therefore, creating the radiation treatment outcome can be a time consuming process that involves multiple medical personnel providing multiple iterations of the treatment outcome over many days, which may increase the time from diagnosis of the cancer to treatment of the cancer. In particular, the dosimetrist who creates the treatment outcome has a difficult challenge in creating the optimal plan due to the overwhelming degrees of freedom and constraint priorities. Further, physicians, who should be guiding the dosimetrist during the treatment planning, are often disconnected from the treatment planning process because of other demands on their time. Consequently, the modern radiation treatment planning process is time-consuming and often proceeds without the sufficient involvement of the physician treating the patient.

SUMMARY

A preliminary stage in radiation treatment planning for a given patient involves a physician defining the contours of the tumor volume and anatomical structures located near the tumor volume. The treatment planning engine described herein empowers radiation treatment decision makers, such as a physician, to efficiently identify an effective radiation treatment outcome for a given patient during the contouring stage. Specifically, the treatment planning engine stores treatment outcomes resulting from radiation treatment delivered to patients over time. Using the treatment planning engine, the physician may iteratively and in real-time evaluate different treatment outcomes of patients determined to be similar to the current patient before selecting an optimal plan for the patient. By providing real-time information as to potential toxicity and treatment efficacy during the contouring stage, the physician is empowered to make informed decisions at the preliminary contouring stage.

In operation, the treatment planning engine enables the physician to easily define contours of tumor volumes and nearby anatomical structures of a given patient. Based on the defined contours, the treatment planning engine identifies treatment outcomes resulting from previously delivered radiation treatment that may be effective for the given patient and provides those treatment outcomes to the physician for evaluation. Each treatment outcome specifies the dose of radiation that was delivered to a tumor volume and/or the nearby anatomical structures. Upon evaluating the identified treatment outcomes, the physician may select one of the outcomes for the patient or may re-define the contours of the tumor volume and nearby anatomical structures such that the treatment planning engine identifies different treatment outcomes according to the new contours. In such a manner, the treatment planning engine allows the physician to iteratively modify the contours until a treatment outcome that delivers the optimal radiation treatment to the patient is identified.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Architecture

Figure 1:
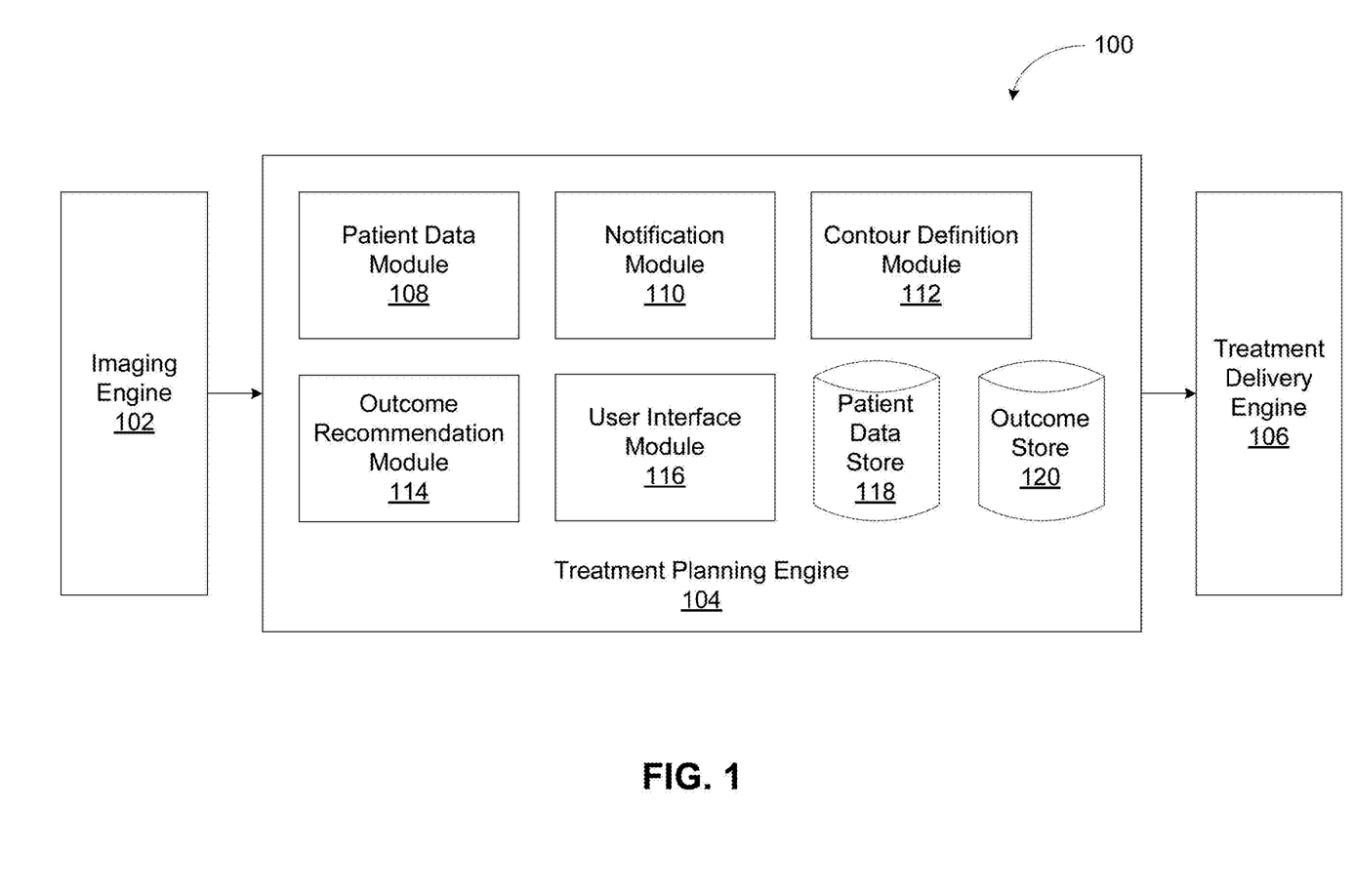
FIG. 1 is a block diagram of a system environment for radiation treatment planning and delivery, in accordance with an embodiment of the invention.

FIG. 1 is a block diagram of a system environment 100 for radiation treatment planning and delivery, in accordance with an embodiment of the invention. As shown, the system environment 100 includes an imaging engine 102, a treatment planning engine 104, and a treatment delivery engine 106.

The imaging engine 102 provides imaging data associated with patients needing radiation treatment. The imaging data may include visual representations of the interior of a patient's body for medical purposes. In one embodiment, the imaging engine 102 generates the visual representation through one or more scanning techniques, such as computed tomography (CT), nuclear medicine including positron emission tomography (PET), and magnetic resonance imaging (MRI). In alternative embodiments, the imaging engine 102 receives the imaging data from external sources and stores the imaging data in an internal data base. The imaging engine 102 transmits the imaging data associated with the patient to the treatment planning engine 104 for the purposes of generating a radiation treatment outcome for the patient.

The treatment planning engine 104 processes imaging data associated with a patient and recommends different treatment outcomes to the patient's physician, thus enabling the physician to efficiently identify the optimal treatment outcome for the patient. The treatment planning engine 104 includes a patient data module 108, a notification module 110, a contour definition module 112, an outcome recommendation module 114, a user interface (UI) module 116, a patient data store 118, and an outcome store 120.

The patient data store 118 and the outcome store 120 may each be, or include, one or more tables, one or more relational databases, and/or one or more multi-dimensional data cubes. Further, though illustrated as a single component, the patient data store 118 and the outcome store 120 may each be a plurality of databases, such as a database cluster, which may be implemented on a single computing device or distributed between a number of computing devices or memory components. Further, the various modules and data stores included in the treatment planning engine 104 may be physically co-located within one computing system or, alternatively, may be disparately located across multiple computing systems.

The patient data module 108 manages patient data and stores such data in the patient data store 118. In one embodiment, each patient has a unique identifier such that the patient data belonging to a given patient is stored in conjunction with the unique identifier. Patient data includes, but is not limited to, imaging data received from the imaging engine 102, electronic medical records (EMRs) associated with the patient, information related to the patient's treatment team (e.g., physician), and the treatment machines (e.g., radiation therapy machine) that is likely to be used for the patient. With regards to imaging data, the patient data module 108 may automatically receive new imaging data from the imaging engine 102 or, alternatively, may periodically request new imaging data from the imaging engine 102.

When new imaging data associated with a patient is stored in the patient data store 118, the notification module 110 transmits a notification to the patient's physician informing the physician that the data is available for further evaluation. In one embodiment, the notification module 110 regularly polls the patient data store 118 for new patient data. In another embodiment, the notification module 110 polls the patient data store 118 for new patient data when a physician accesses the treatment planning engine 104 to determine whether new imaging data has been received for any of the physician's patients. The notification transmitted to the physician may be an email, a message transmitted over a short messaging service, or a push notification transmitted to the physician via a mobile application. The notification may include a link to automatically launch the contour definition module 112.

The contour definition module 112 detects the contours identifying the three-dimensional tumor volumes captured in the imaging data and the anatomical structures located in the same region as the tumor volumes. The contour definition module 112 may automatically generate contours of the tumor volume and anatomical structures using contouring techniques known in the field. In addition, the contour definition module 112 may automatically generate contours of the tumor volume and anatomical structures using historical contours created for the current patient or a different patient having similar imaging data stored in the patient data store 118.

The contour definition module 112 may provide suggested contours to the physician based on previously created contours stored in the patient data store 118. The contour definition module 112 determines the suggested contours by comparing the image data associated with the current patient with image data for which contours were previously determined and stored in the patient data store 118. When the image data associated with the current patient is statistically similar to image data stored in the patient data store 118, the contour definition module 112 suggests the previously determined contours for the statistically similar image data to the physician. In operation, the contour definition module 112 leverages the outcome recommendation module 114, i.e., the mapping between contours and treatment outcomes, to provide the statistical basis for providing alternate contours for the tumor volume and the neighboring anatomical structures (also referred to herein as the "planning tumor volume (PTV)"). In this embodiment, the contour definition module 112 utilizes definitions of the gross tumor volume (GTV) and/or clinical tumor volume (CTV), where the physician (or alternatively an automated algorithm) contours what is determined with high-confidence to be tumor. This GTV or CTV contour is the minimum suggested PTV size. A treatment outcome is created from this minimum accepted PTV size based on the mappings between contours and treatment outcomes 114. The contour definition module 112 then creates series of uniform or non-uniform expansions of the PTV and maps these expansions of the PTV to outcomes based on the outcome results provided by the outcome recommendation module 114.

To reduce the potential number of contour suggestions, the contour definition module 112 may be configured with a threshold such that only contours that result in changes to treatment outcomes exceeding the threshold are presented to the physician. Similarly, if a suggested contour results in a treatment outcome that is statistically similar to a contour of a previously treated patient, this contour may be presented with an additional indication that it matches a previous patient.

In one embodiment, a metric of similarity may be Euclidean distance between predicted treatment outcomes (as output by the outcome recommendation module 114) and the previously-treated patient outcomes, or other distance-based metrics known in the art. A preferred method to calculate this distance-based similarity metric, S, is through the method of least squares between the predicted dose to the new patient based on each contour expansion, Dnew, and the dose given to a previous patient, Dprev:

$$S=\sqrt{(D_{new}-D_{prev})^2}.$$

In this preferred method, if S is less than the threshold, the contour is recommended. Here, the threshold may be chosen manually (based on physician-preferred fidelity), or may be learned from the variation in predicted outcomes across the cross-validated kth model constructed from the kth fold of the training data set. If the physician chooses to accept a suggested contour, then the predicted treatment outcome is presented to the physician.

Figure 2:
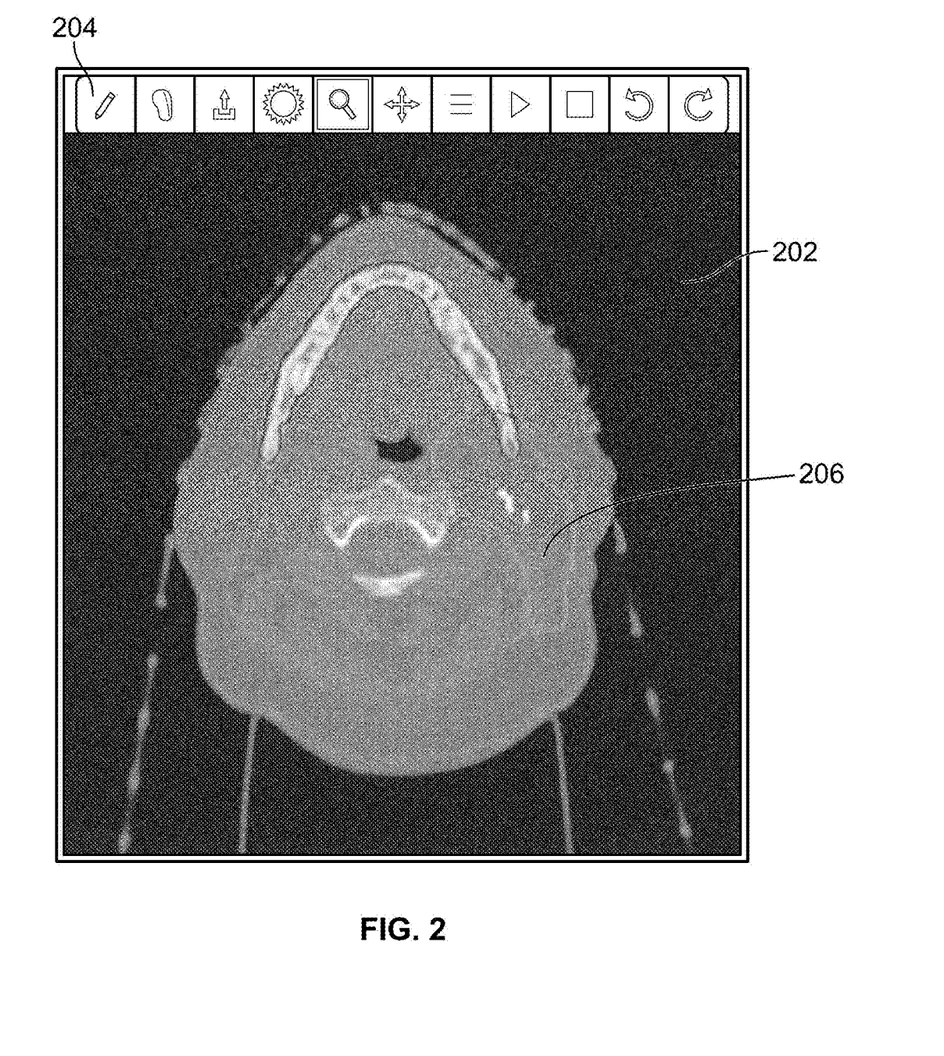
FIG. 2 is an exemplary user interface for defining contours on patient image data, in accordance with an embodiment of the invention.

The contour definition module 112 also enables the physician to manually create and/or edit the contours of the tumor volume and anatomical structures. In operation, the contour definition module 112 provides a graphical user interface that includes a visual representation of the imaging data associated with the patient and one or more contouring tools that allow the physician to create or edit contours. FIG. 2 is an exemplary user interface for defining contours on patient image data, in accordance with an embodiment of the invention. As shown, the user interface includes a visual representation 202 of imaging data associated with a given patient. The user interface also includes contouring controls 204 that enable a physician to draw the contours around tumor volumes and neighboring anatomical structures. In the illustrated example, the region 206 is enclosed by a contour manually created by the physician using the contouring controls 204.

Returning to FIG. 1, as the contour definition module 112 detects contours (automatically or manually defined), the contour definition module 112 transmits requests to the outcome recommendation module 114 to generate recommended treatment outcomes for the current patient based on the detected contours. The outcome recommendation module 114 performs a multi-feature comparative analysis between the current patient and previous patients to identify previously-administered treatment outcomes stored in the outcome store 120 that are applicable to the current patient.

The outcome store 120 stores information associated with previous treatment outcomes such as, for example, previously planned radiation treatments that were approved for use on patients by medical personnel, or previously planned radiation treatments that were used on patients by medical personnel. In one embodiment, each treatment outcome specifies the dose of radiation that was administered to tumor volumes and any neighboring anatomical structure during the radiation treatment. In another embodiment, each treatment outcome specifies a probability of control for tumor volumes and/or probability of toxicity for any neighboring anatomical structure resulting from the radiation treatment. The outcome store 120 may also include a medical data database that includes medical data associated with the previously planned radiation treatments. In some embodiments, the outcome store 120 includes a processed database configured to store selected data that have been extracted and transformed from a medical data database and stored in the processed database.

The outcome recommendation module 114 compares features extracted from patient data associated the current patient with features and/or outcomes extracted from data associated with other patients, as stored in the patient data store 118, to identify recommended treatment outcomes for the current patient. The features associated with patient data may include a physics parameter, a treatment type parameter, a patient image parameter, and/or a disease parameter. In one embodiment, physics parameters may be, or include, penumbra, aperture, incident angle, beam energy, radiation type, depth of structure, and/or existence of bolus. Treatment type parameters may be, or include, fractionation schedule, treatment margin, number of beams/arcs, interpretation of contours, and/or the clinicians who are part of the team creating the radiation treatment outcome. Patient image parameters may be, or include, distance, volume, geometric relationship, and/or the importance of structures and surrounding structures. Disease parameters may be, or include, disease stage, prior or post treatment therapy, prior radiation therapy, prior radiation damage to nearby tissue, disease type, disease histology, extent of the disease, and/or prior disease.

Any number of different types of techniques and/or algorithms may be utilized to identify the recommended treatment outcomes by comparing features of the current patient with previous patients, and may include statistical techniques, pattern-matching techniques, artificial intelligence techniques, and/or the like. In some embodiments, the outcome recommendation module 114 may include a search engine, a query module, and/or a database management component. Identifying previously administered treatment outcomes based on a multi-feature comparative analysis, as performed by the outcome recommendation module 114 may be performed with the techniques described above, and is further described in U.S. patent application Ser. No. 14/310,925, filed on Jun. 20, 2014, which is hereby incorporated by reference in its entirety.

The outcome recommendation module 114 presents the recommended treatment outcomes for the current patient to the physician via the user interface (UI) module 116. The UI module 116 generates a visual representation of each recommended treatment outcome. In one embodiment, the UI module 116 associates different visual indicators with the radiation doses delivered during the execution of the treatment outcome. As discussed above, each treatment outcome specifies the dose of radiation treatment delivered to one or more tumor volumes and nearby anatomical structures. For each tumor volume or anatomical structure, the UI module 116 determines a visual indicator for the corresponding dose based on the risk level associated with the dose. When the treatment outcome specifies a dose that delivers a larger than recommended amount of radiation to an organ at risk, the visual representation of the dose to that organ may be highlighted or color coded to represent the high risk. Conversely, when the treatment outcome specifies a dose that delivers an acceptable amount of radiation to an organ at risk, the visual representation of the dose to that organ may be highlighted or color coded to represent the relatively lower risk. Such visual indicators enable the physician viewing and evaluating the recommended treatment outcomes to quickly determine whether a given treatment outcome is optimal for the current patient.

Figure 3:
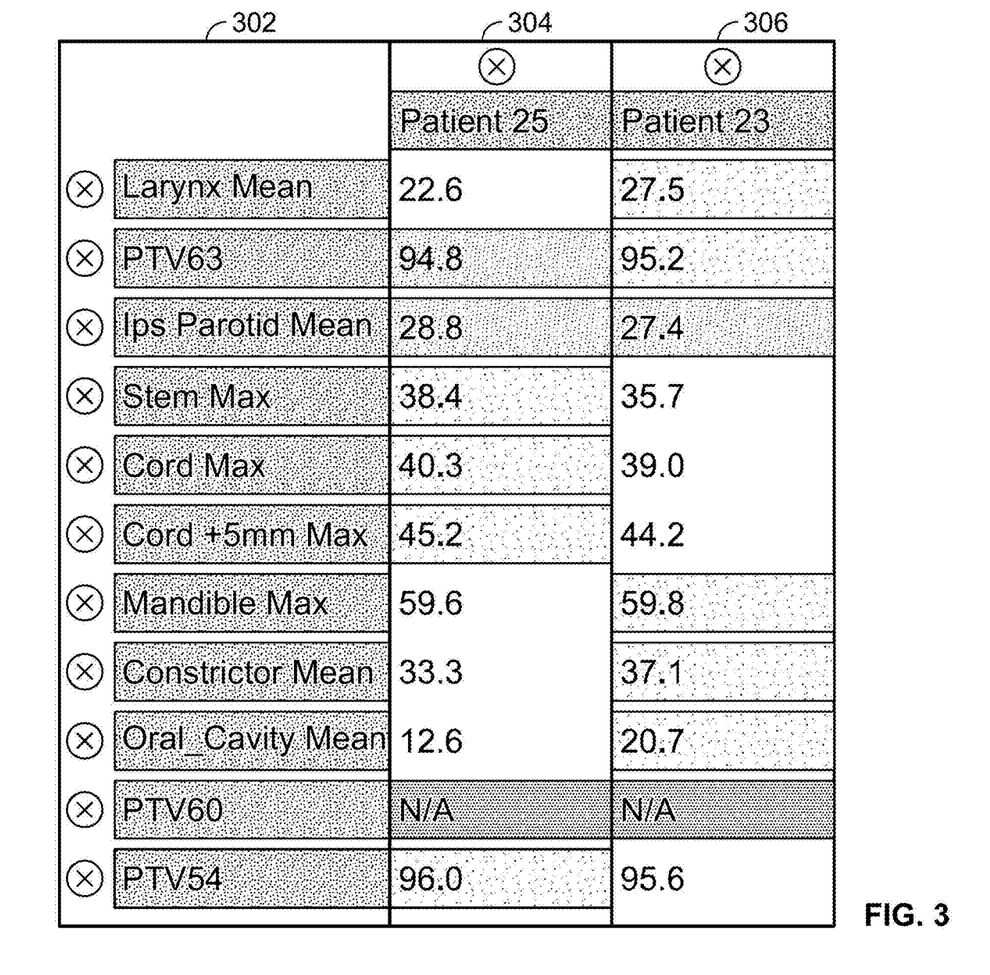
FIG. 3 is an exemplary user interface for visualizing recommended treatment outcomes, in accordance with an embodiment of the invention.

FIG. 3 is an exemplary user interface generated by the UI module 116 for providing visual representations of recommended treatment outcomes, in accordance with an embodiment of the invention. As shown, the user interface includes a structure column 302 that lists each of the structures and tumors identified by the contour. The user interface also includes one or more outcome columns, such as outcome column 304 and outcome column 306. Each outcome column is associated with a different recommended treatment outcome and lists, for each structure and tumor in the structure column 302, the dose of radiation, if any, to be delivered per the treatment outcome. Further, as illustrated, the doses of radiation in the outcome columns are color based on the risk level associated with the dose.

Returning to FIG. 2, upon evaluating the recommended treatment outcomes, the physician may select one of the recommended treatment outcomes via a control provided by the user interface module 116. Alternatively, when none of the recommended outcomes is deemed optimal by the physician, the physician may edit the contours of the tumor volume and neighboring anatomical structures via the contour definition module 112. In response to the contours being edited, the contour definition module 112 transmits another request to the outcome recommendation module 114 to generate new recommended treatment outcomes that are subsequently presented to the physician.

In such a paradigm, the physician is able to adjust contours and in real-time evaluate the impact on the tumor volume and the toxicity risk to the nearby anatomical structures. When the physician is satisfied with a given recommended outcome, the physician selects the treatment outcome for the current patient. In response, the outcome recommendation module 114 stores the contour in conjunction with the selected treatment outcome in the patient data store 118. In addition, the outcome recommendation module 114 transmits a notification to the treatment delivery engine 106 indicating that the physician has selected a treatment outcome for the patient.

The treatment delivery engine 106 enables a dosimetrist or physicist to create a patient-specific treatment delivery plan based on the treatment outcome selected by the physician ("the selected treatment outcome"). In operation, the treatment delivery engine 106 transmits a notification, such as an email or a push notification on a mobile application, to the dosimetrist or physicist indicating that the physician selected a treatment outcome for the patient. The notification may optionally include a representation of the selected treatment outcome and/or a link to access the selected treatment outcome. The dosimetrist or physicist evaluates the selected treatment outcome and creates a treatment delivery plan that is specific to the patient. Specifically, the selected treatment outcome informs the dosimetrist or physicist of the clinically appropriate profile of radiation to be delivered including but not limited to radiation intensity, angle of delivery, multi-leaf collimator status, temporal fractionation, anatomy, presentation of the tumor, anticipated treatment outcomes, prior clinical staff, and anticipated treatment course.

Based on the treatment delivery plan, the treatment delivery engine 106 generates a patient-specific delivery template that configures a radiation therapy machine for delivering the radiation treatment to the patient. In one embodiment, the treatment delivery engine 106 interacts with a therapy machine control interface that is configured with standard communication protocols. The patient-specific delivery template identifies the tumor volumes as well as the anatomical structures that are to receive radiation treatment. For each volume or structure, the delivery template may also specify the percentage volume that is to receive radiation treatment and the dose of treatment to be delivered. In addition, this template may specify the optimization objectives, treatment protocols, beam orientations, collimator/multi-leaf collimator positions, couch positions, and other parameters known in the art. Table 1 illustrates an exemplary patient-specific delivery template.

TABLE 1

| Critical Structures | Dose Volume | Type of constraint | Dose Constraint | Priority |
| --- | --- | --- | --- | --- |
| PTV 63 | 95.39 | Lower | 63 | 120.0 |
| PTV 60 | 93.97 | Lower | 60 | 120.0 |
| PTV 54 | 95.22 | Lower | 54 | 120.0 |
| IPSeyemax | 0 | Upper | 1.78 | 50.0 |
| CONTRAeyemax | 0 | Upper | 1.5 | 50.0 |
| IPSOPTICNRVmax | 0 | Upper | 2.13 | 50.0 |
| CONTRAOPTICNRVmax | 0 | Upper | 1.5 | 50.0 |
| TS_IPSPAROTIDmax | 0 | Upper | 66.86 | 90.0 |
| TS_CONTRAPAROTIDmax | 0 | Upper | 59.19 | 90.0 |
| IPSMIDEARmean | | Mean | 8.3 | 50.0 |
| CONTRAMIDEARmean | | Mean | 4.86 | 50.0 |
| IPSPAROTIDmean | | Mean | 29.68 | 120.0 |
| CONTRAPAROTIDmean | | Mean | 15.66 | 90.0 |
| IPSLOBEmean | | Mean | 2.38 | 50.0 |
| CONTRALOBEmean | | Mean | 1.63 | 50.0 |
| CONTRASALVmean | | Mean | 35.63 | 90.0 |

Physician Directed Treatment Planning

Figure 4:
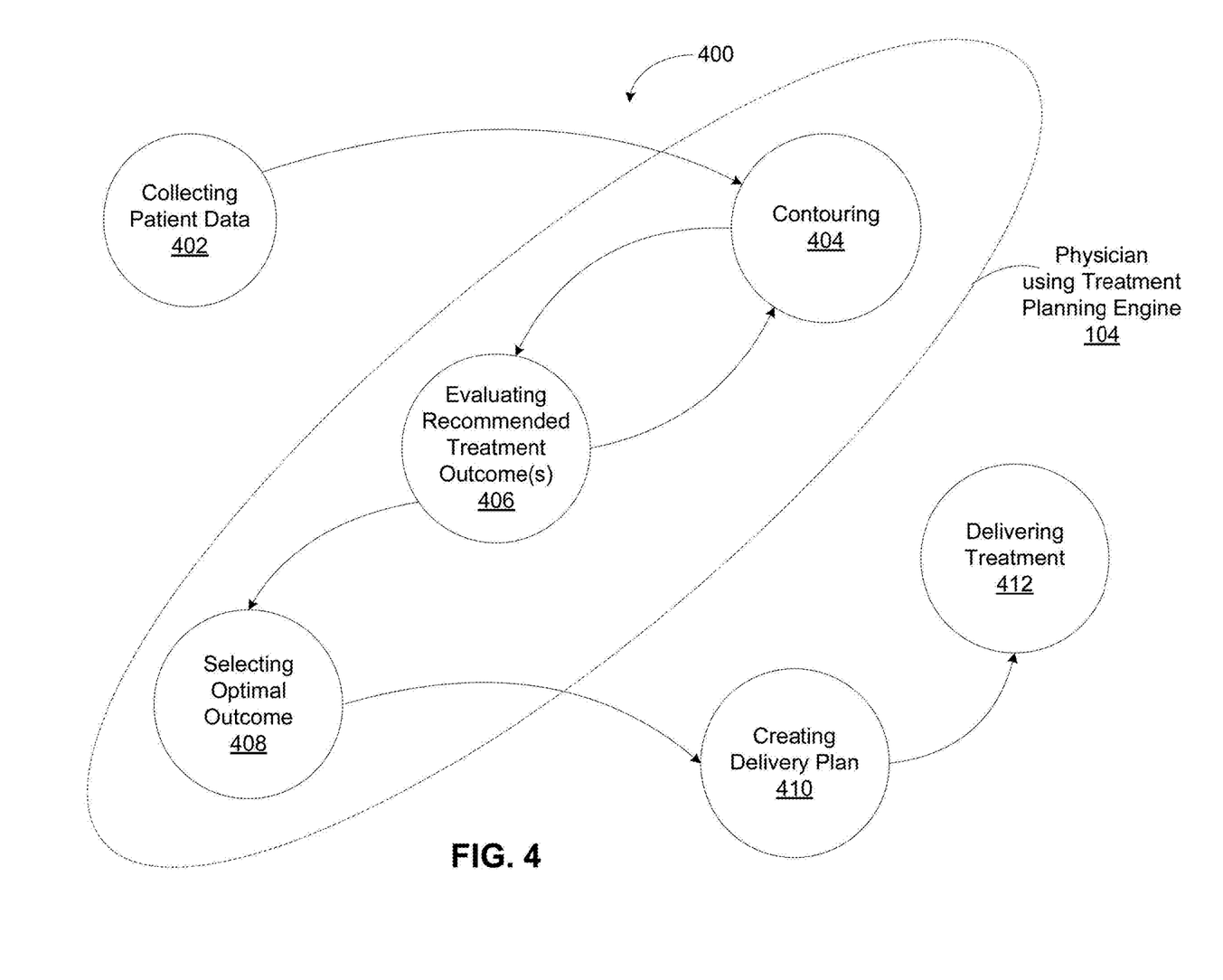
FIG. 4 is a state diagram illustrating the various stages of radiation treatment planning and delivery, in accordance with an embodiment of the invention.

The treatment planning engine 104 enables physician directed treatment planning where the physician is able to adjust contours around the tumor volume and in real-time or near real-time evaluate the impact on the tumor volume and the toxicity risk to the nearby anatomical structures. FIG. 4 is a state diagram 400 illustrating the various stages of physician directed radiation treatment planning using the treatment planning engine 104, in accordance with an embodiment of the invention. In state 402, patient data associated with a patient who is to receive radiation treatment is collected. Such patient data may include imaging data, electronic medical records and information related to the anticipated therapy system. In state 404, the patient's physician, using the contour definition module 112, defines the contours of the tumor volumes and/or the anatomical structures included in the imaging data that are to receive radiation treatment. In state 406, the physician evaluates recommended treatment outcomes recommended by the outcome recommendation engine 114 to determine whether any of the treatment outcomes are suitable for the patient. The physician iterates through states 404 and 406 until the outcome recommendation engine 114 presents a suitable treatment outcome. In state 408, the physician selects the treatment outcome for the patient via the outcome recommendation engine 114, which transmits a notification to the dosimetrist. In state 410, the dosimetrist evaluates the selected treatment outcome and creates a treatment delivery plan that is specific to the patient. In state 412, a radiation therapy machine delivers radiation treatment to the patient based on the delivery plan created by the dosimetrist.

Figure 5:
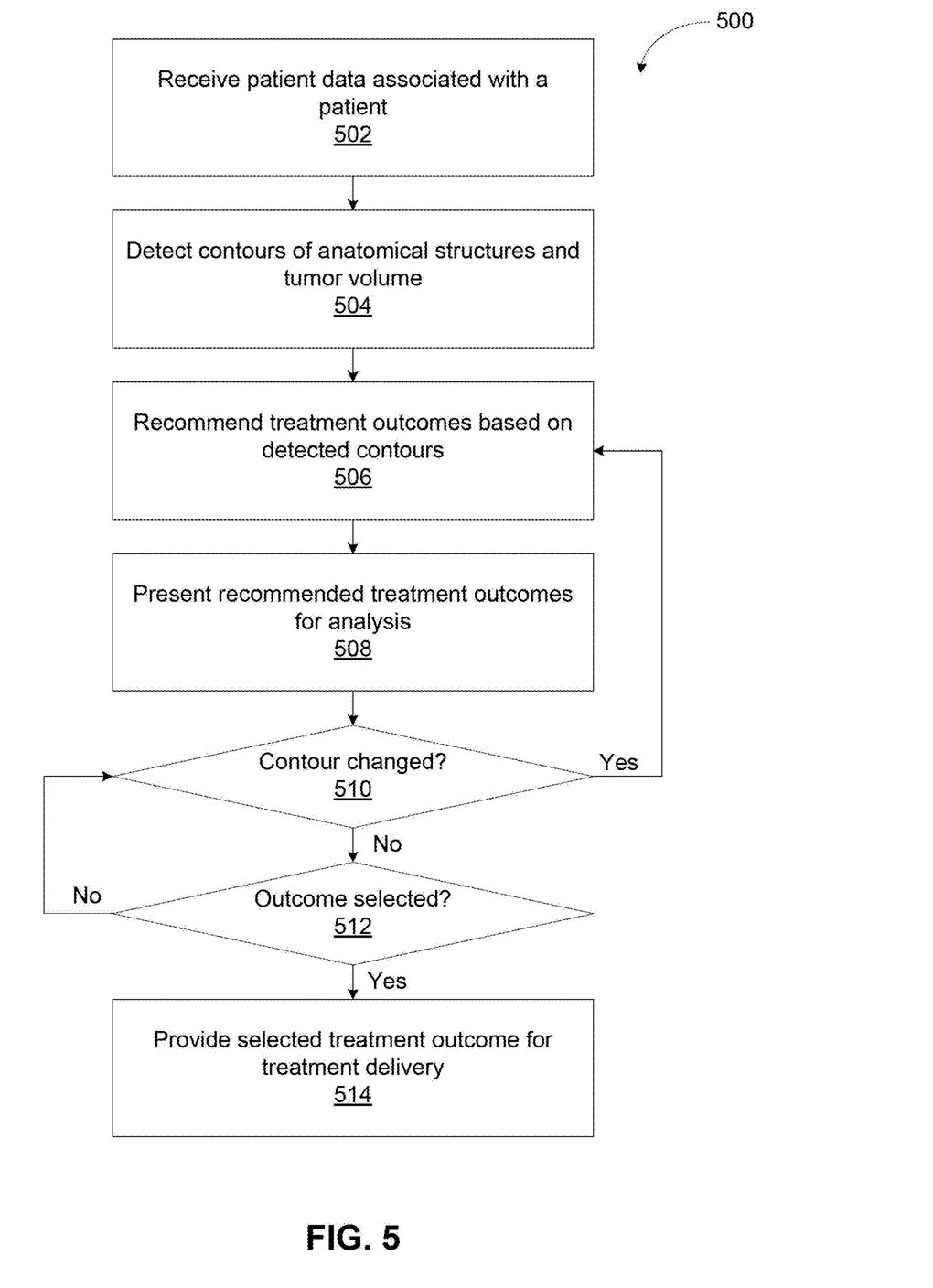
FIG. 5 is a flow diagram illustrating the steps for physician directed radiation treatment planning, in accordance with an embodiment of the invention.

FIG. 5 is a flow diagram 500 illustrating the steps for physician directed radiation treatment planning, in accordance with an embodiment of the invention. Other embodiments may perform the steps of the process illustrated in FIG. 5 in different orders and can include different, additional and/or fewer steps. The process may be performed by any suitable entity, such as the treatment planning engine 104.

The treatment planning engine 104 receives 502 patient data, including, but not limited to, imaging data, data accumulated from the medical record, associated with a patient, and information related to the anticipated therapy system. The treatment planning engine 104 may automatically receive imaging data from the imaging engine 102 or, alternatively, may periodically request imaging data from the imaging engine 102. Imaging data associated with a patient includes visual representations of the interior of a patient's body or a portion thereof. The treatment planning engine 104 detects 504, based on the imaging data, contours identifying the three-dimensional tumor volumes and the anatomical structures near the tumor volumes. In one embodiment, the treatment planning engine 104 enables the patient's physician to create and/or edit the contours of the tumor volume and anatomical structures via a graphical user interface. In alternate embodiments, the treatment planning engine 104 automatically creates the contours using pre-existing contouring techniques.

The treatment planning engine 104 recommends 506 treatment outcomes for the patient based on the detected contours. In one embodiment, the treatment planning engine 104 performs a multi-feature comparative analysis between the current patient and previous patients to identify treatment outcomes stored in the outcome store 120 that are applicable to the current patient. The treatment planning engine 104 presents 508 the recommended treatment outcomes to the physician via a user interface that generates a visual representation of each recommended treatment outcome.

The treatment planning engine 104 determines 510 whether the contour identifying the three-dimensional tumor volumes and the anatomical structures has changed. Specifically, the physician may edit the contour using one or more contouring tools. If the contour changes, then the treatment planning engine 104 re-computes 506 new treatment outcome recommendations based on the updated contours. If the contour does not change, then the treatment planning engine 104 determines 512 whether the physician selected a given recommended treatment outcome. The treatment planning engine 104 continues to loop through 510-512 until the physician selects a plan.

When the patient selects a treatment outcome, the treatment planning engine 104 provides 514 the selected treatment outcome to the treatment delivery engine 106 for the purposes of delivering radiation treatment to the patient according to the selected outcome. The treatment delivery engine 106 enables a dosimetrist or physicist to create a patient-specific treatment delivery plan based on the treatment outcome selected by the physician.

Example Computer System

Figure 6:
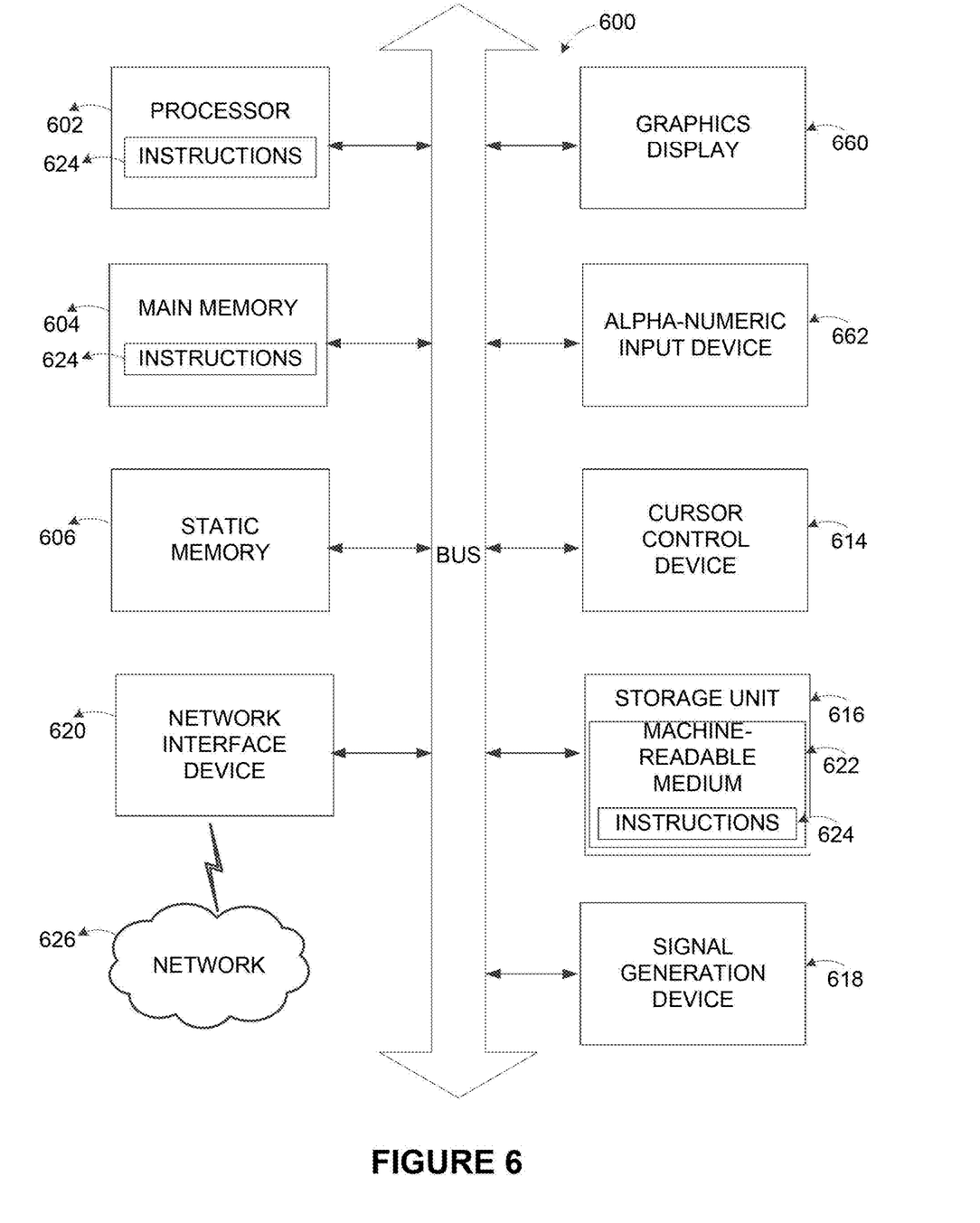
FIG. 6 is a block diagram illustrating components of an example machine configured to read instructions from a machine-readable medium and execute the instructions in a processor (or controller), in accordance with an embodiment of the invention.

FIG. 6 is a block diagram illustrating components of an example machine able to read instructions from a machine-readable medium and execute them in a processor (or controller). The computer system 600 can be used to execute instructions 624 (e.g., program code or software) for causing the machine to perform any one or more of the methodologies (or processes) described herein. In alternative embodiments, the machine operates as a standalone device or a connected (e.g., networked) device that connects to other machines. In a networked deployment, the machine may operate in the capacity of a server machine or a client machine in a server-client network environment, or as a peer machine in a peer-to-peer (or distributed) network environment. Each of the various engines and modules described herein may be implemented using all or some of the components of the computer system 600.

The machine may be a server computer, a client computer, a personal computer (PC), a tablet PC, a set-top box (STB), a smartphone, an internet of things (IoT) appliance, a network router, switch or bridge, or any machine capable of executing instructions 624 (sequential or otherwise) that specify actions to be taken by that machine. Further, while only a single machine is illustrated, the term "machine" shall also be taken to include any collection of machines that individually or jointly execute instructions 624 to perform any one or more of the methodologies discussed herein.

The example computer system 600 includes one or more processing units (generally processor 602). The processor 602 is, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of these. The computer system 600 also includes a main memory 604. The computer system may include a storage unit 616. The processor 602, memory 604 and the storage unit 616 communicate via a bus 608.

In addition, the computer system 600 can include a static memory 606, a display driver 660 (e.g., to drive a plasma display panel (PDP), a liquid crystal display (LCD), or a projector). The computer system 600 may also include an alphanumeric input device 662 (e.g., a keyboard), a cursor control device 614 (e.g., a mouse, a trackball, a joystick, a motion sensor, or other pointing instrument), a signal generation device 618 (e.g., a speaker), and a network interface device 620, which also are configured to communicate via the bus 608.

The storage unit 616 includes a machine-readable medium 622 on which is stored instructions 624 (e.g., software) embodying any one or more of the methodologies or functions described herein. The instructions 624 may also reside, completely or at least partially, within the main memory 604 or within the processor 602 (e.g., within a processor's cache memory) during execution thereof by the computer system 600, the main memory 604 and the processor 602 also constituting machine-readable media. The instructions 624 may be transmitted or received over a network 626 via the network interface device 620.

While machine-readable medium 622 is shown in an example embodiment to be a single medium, the term "machine-readable medium" should be taken to include a single medium or multiple media (e.g., a centralized or distributed database, or associated caches and servers) able to store the instructions 624. The term "machine-readable medium" shall also be taken to include any medium that is capable of storing instructions 624 for execution by the machine and that cause the machine to perform any one or more of the methodologies disclosed herein. The term "machine-readable medium" includes, but not be limited to, data repositories in the form of solid-state memories, optical media, and magnetic media.

CONCLUSION

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for creating a radiation treatment plan for a given patient, the method comprising:
    receiving imaging data that includes a representation of an interior of a patient who is to receive radiation treatment;
    displaying the received imaging data in a user interface;
    performing a treatment planning process for the patient, the treatment planning process comprising:
        detecting a contour identifying one or more anatomical structures and at least one tumor volume represented by the imaging data,
        computing a set of recommended treatment outcomes for the patient based on the contour and previously administered treatment outcomes, wherein each recommended treatment outcome comprises a corresponding set of radiation doses to be delivered to at least a subset of the one or more anatomical structures, and
        presenting in a user interface the set of recommended treatment outcomes to a physician for evaluation, wherein, for a first recommended treatment outcome presented in the user interface, the user interface includes a first visual indicator having a first color, wherein the first color is determined based on at least one radiation dose corresponding to the first recommended treatment outcome;
    receiving a selection from the physician of a given recommended treatment outcome; and
    providing the selected treatment outcome to a system for generating a treatment plan for the patient that achieves the selected outcome.

2. The method of claim 1, wherein the first color is determined based on a risk level associated with the at least one radiation dose.

3. The method of claim 1, wherein the first color is determined based on a magnitude of the at least one radiation dose.

4. The method of claim 1, wherein detecting the contour comprises determining that at least one previously-detected contour has been edited and detecting at least one new contour identifying the one or more anatomical structures or the at least one tumor volume represented by the imaging data.

5. The method of claim 1, wherein detecting the contour comprises providing a contouring interface to the physician that enables the physician to manually define the contour on a visual representation of the imaging data.

6. The method of claim 1, wherein detecting the contour comprises automatically determining the contour based on a previously-created contour associated with second imaging data.

7. The method of claim 1, wherein detecting the contour comprises:
    generating one or more expansions of a minimum tumor volume definition provided by the physician;
    identifying a subset of the previously administered treatment outcomes that map to at least one of the one or more expansions of the minimum tumor volume definition; and
    suggesting an alternative contour associated with a first treatment outcome included in the subset of the previously administered treatment outcomes.

8. The method of claim 7, wherein suggesting the alternative contour comprises:
    comparing the first treatment outcome with a given recommended treatment outcome of the set of recommended treatment outcomes;
    determining that a difference between the first treatment outcome and the given recommended treatment outcome is greater than a threshold difference; and
    selecting the first treatment outcome for contour suggestion.

9. The method of claim 1, wherein computing the set of recommended treatment outcomes comprises comparing features extracted from patient data associated with the patient with features extracted from treatment outcomes previously administered to other patients.

10. The method of claim 1, wherein presenting the set of recommended treatment outcomes comprises, for each recommended treatment outcome, generating a visual representation that specifies a different radiation dose to be delivered to each of the one or more anatomical structures and the at least one tumor volume.

11. The method of claim 1, wherein providing the selected treatment outcome comprises generating a patient-specific delivery template that configures a radiation therapy machine for delivering radiation treatment to the patient.

12. A computer program product for creating a radiation treatment plan for a patient, the computer program product comprising a non-transitory computer-readable storage medium containing computer program code for:
    receiving imaging data that includes a representation of an interior of a patient who is to receive radiation treatment;
    displaying the received imaging data in a user interface;
    performing a treatment planning process for the patient, the treatment planning process comprising:
        detecting a contour identifying one or more anatomical structures and at least one tumor volume represented by the imaging data,
        computing a set of recommended treatment outcomes for the patient based on the contour and previously administered treatment outcomes, wherein each recommended treatment outcome comprises a corresponding set of radiation doses to be delivered to at least a subset of the one or more anatomical structures, and
        presenting in a user interface the set of recommended treatment outcomes to a physician for evaluation, wherein, for a first recommended treatment outcome presented in the user interface, the user interface includes a first visual indicator having a first color, wherein the first color is determined based on at least one radiation dose corresponding to the first recommended treatment outcome;
    receiving a selection from the physician of a given recommended treatment outcome; and
    providing the selected treatment outcome to a system for generating a treatment plan for the patient that achieves the selected outcome.

13. The computer program product of claim 12, wherein the first color is determined based on a risk level associated with the at least one radiation dose.

14. The computer program product of claim 12, wherein the first color is determined based on a magnitude of the at least one radiation dose.

15. The computer program product of claim 12, wherein detecting the contour comprises determining that at least one previously-detected contour has been edited and detecting at least one new contour identifying the one or more anatomical structures or the at least one tumor volume represented by the imaging data.

16. The computer program product of claim 12, wherein detecting the contour comprises providing a contouring interface to the physician that enables the physician to manually define the contour on a visual representation of the imaging data.

17. The computer program product of claim 12, wherein detecting the contour comprises automatically determining the contour based on a previously-created contour associated with second imaging data.

18. The computer program product of claim 12, wherein detecting the contour comprises:
generating one or more expansions of a minimum tumor volume definition provided by the physician;
identifying a subset of the previously administered treatment outcomes that map to at least one of the one or more expansions of the minimum tumor volume definition; and
suggesting an alternative contour associated with a first treatment outcome included in the subset of the previously administered treatment outcomes.

19. The computer program product of claim 18, wherein suggesting the alternative contour comprises:
comparing the first treatment outcome with a given recommended treatment outcome of the set of recommended treatment outcomes; and
determining that a difference between the first treatment outcome and the given recommended treatment outcome is greater than a threshold difference.

20. The computer program product of claim 12, wherein computing the set of recommended treatment outcomes comprises comparing features extracted from patient data associated with the patient with features extracted from treatment outcomes previously administered to other patients.

21. The computer program product of claim 12, wherein presenting the set of recommended treatment outcomes comprises, for each recommended treatment outcome, generating a visual representation that specifies a different radiation dose to be delivered to each of the one or more anatomical structures and the at least one tumor volume.

22. A system for creating a radiation treatment plan for a patient, the system comprising:
a memory storing instructions;
a processor for executing the instructions to:
receive imaging data that includes a representation of an interior of a patient who is to receive radiation treatment;
display the received imaging data in a user interface;
perform a treatment planning process for the patient, the treatment planning process comprising:
detect a contour identifying one or more anatomical structures and at least one tumor volume represented by the imaging data,
compute a set of recommended treatment outcomes for the patient based on the contour and previously administered treatment outcomes, wherein each recommended treatment outcome comprises a corresponding set of radiation doses to be delivered to at least a subset of the one or more anatomical structures, and
present in a user interface the set of recommended treatment outcomes to a physician for evaluation, wherein, for a first recommended treatment outcome presented in the user interface, the user interface includes a first visual indicator having a first color, wherein the first color is determined based on at least one radiation dose corresponding to the first recommended treatment outcome;
receive a selection from the physician of a given recommended treatment outcome; and
provide the selected treatment outcome to a system for generating a treatment plan for the patient that achieves the selected outcome.

23. The system of claim 22, wherein the first color is determined based on a risk level associated with the at least one radiation dose.

24. The system of claim 22, wherein the first color is determined based on a magnitude of the at least one radiation dose.

* * * * *